US006593395B2

(12) United States Patent
Angeletakis et al.

(10) Patent No.: US 6,593,395 B2
(45) Date of Patent: Jul. 15, 2003

(54) DENTAL COMPOSITION CONTAINING DISCRETE NANOPARTICLES

(75) Inventors: Christos Angeletakis, Orange, CA (US); Minh-Dang Son Nguyen, Orange, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 09/859,106

(22) Filed: May 16, 2001

(65) Prior Publication Data

US 2002/0193462 A1 Dec. 19, 2002

(51) Int. Cl.⁷ .......................... A61K 6/083; C08K 3/22; C08K 3/34; A61C 13/08
(52) U.S. Cl. ...................... 523/115; 523/113; 523/116; 523/118; 524/430; 524/444; 433/202.1; 433/226
(58) Field of Search ............................... 433/202.1, 226; 523/113, 115, 116, 118; 524/430, 444

(56) References Cited

U.S. PATENT DOCUMENTS

| 4,503,169 A | | 3/1985 | Randklev ..................... 523/117 |
|---|---|---|---|
| 5,192,815 A | * | 3/1993 | Okada et al. ................. 523/115 |
| 5,460,701 A | | 10/1995 | Parker et al. ................. 204/164 |
| 5,514,349 A | | 5/1996 | Parker et al. .......... 422/186.21 |
| 5,610,712 A | | 3/1997 | Schmitz et al. .............. 356/335 |
| 5,788,738 A | | 8/1998 | Pirzada et al. ................. 75/331 |
| 5,851,507 A | | 12/1998 | Pirzada et al. ............... 423/659 |
| 5,874,684 A | | 2/1999 | Parker et al. .................. 75/228 |
| 5,936,006 A | | 8/1999 | Rheinberger et al. ....... 523/116 |
| 5,979,805 A | | 11/1999 | Angeletakis .................. 241/21 |
| 5,984,997 A | | 11/1999 | Bickmore et al. ............. 75/343 |
| 6,010,085 A | | 1/2000 | Angeletakis .................. 241/21 |
| 6,098,906 A | | 8/2000 | Angeletakis .................. 241/21 |
| 6,121,344 A | * | 9/2000 | Angeletakis et al. ......... 523/116 |
| 6,127,450 A | | 10/2000 | Angeletakis ................. 523/116 |
| 6,194,481 B1 | | 2/2001 | Furman et al. ................ 522/77 |
| 6,196,843 B1 | * | 3/2001 | Kawaguchi et al. ...... 433/212.1 |
| 6,232,367 B1 | | 5/2001 | Kobashigawa et al. ..... 523/116 |
| 6,300,390 B1 | | 10/2001 | Angeletakis ................. 523/116 |
| 6,306,927 B1 | | 10/2001 | Blackwell et al. .......... 523/116 |
| 6,359,090 B1 | | 3/2002 | Angeletakis ................. 526/277 |

FOREIGN PATENT DOCUMENTS

| EP | 1 050 291 | | 11/2000 | |
|---|---|---|---|---|
| WO | WO 99/65453 | | 12/1999 | |
| WO | WO 00/61073 | | 10/2000 | |
| WO | WO 01/26611 | | 4/2001 | |
| WO | WO 01/30304 | | 5/2001 | |
| WO | WO 01 30304 | * | 5/2001 | .......... A61K/6/083 |
| WO | WO 01/30305 | | 5/2001 | |
| WO | WO 01/30306 | | 5/2001 | |
| WO | WO 01/30307 | | 5/2001 | |

* cited by examiner

Primary Examiner—Tae H. Yoon
(74) Attorney, Agent, or Firm—Wood, Herron & Evans, LLP

(57) ABSTRACT

The present invention provides a dental composite which has the high strength required for load-bearing restorations, yet maintains a glossy appearance, even after substantial wear. Through the use of particles having a mean particle size between about 0.05 μm and about 0.50 μm, the composite is useful in stress bearing restorations and in cosmetic restorations. The structural filler used is typically ground to a mean particle size of less than 0.5 μm and also includes a nanofiller having discrete particles of a mean particle size less than 100 nm to improve handling and mechanical characteristics. The preferred dental composites maintain their surface finish even after substantial use and also have the strength properties of hybrid composite resins.

15 Claims, No Drawings

DENTAL COMPOSITION CONTAINING DISCRETE NANOPARTICLES

FIELD OF THE INVENTION

The present invention is generally related to a composite resin material used for dental restoration, and more particularly to a universal composite resin material suitable for all dental restorations incorporating a uniformly dispersed nanometer sized discrete particulate filler which provides high strength, improved wear resistance and gloss retention in clinical use.

BACKGROUND OF THE INVENTION

In dentistry, practitioners use a variety of restorative materials in order to create crowns, veneers, direct fillings, inlays, onlays and splints. Composite resins are a type of restorative material which are suspensions of strengthening agents, such as mineral filler particles, in a resin matrix. These materials may be dispersion reinforced, particulate reinforced, or hybrid composites.

Dispersion reinforced composites include a reinforcing filler of, for example, fumed silica having a mean particle size of about 0.05 µm or less, with a filler loading of about 30%–45% by volume. Because of the small particle size and high surface area of the filler, the filler loading into the resin is limited by the ability of the resin to wet the filler. Consequently, the filler loading is limited to about 45% by volume. Due to the low loading, the filler particles are not substantially in contact with one another. Thus, the primary reinforcing mechanism of such dispersion reinforced composites is by dislocation of flaws in the matrix around the filler. In dispersion reinforced materials, the strength of the resin matrix contributes significantly to the total strength of the composite. In dentistry, dispersion reinforced composite resins or microfills are typically used for cosmetic restorations due to their ability to retain surface luster. Typically, these microfill resins use free radical-polymerizable resins such as methacrylate monomers, which, after polymerization, are much weaker than the dispersed filler. Despite the dispersion reinforcement, microfill resins are structurally weak, limiting their use to low stress restorations.

One example of a dispersion reinforced composite is HELIOMOLAR®, which is a dental composite including fumed silica particles on the order of 0.05 µm mean particle size and rare earth fluoride particle on the order of less than 0.2 µm mean particle size. HELIOMOLAR® is a radiopaque microfill-type composite. The rare earth fluoride particles contribute to both flexural strength and radiopacity.

Particulate reinforced composites typically include a reinforcing filler having an average particle size greater than about 0.6 µm and a filler loading of about 60% by volume. At these high filler loadings, the filler particles begin to contact one another and contribute substantially to the reinforcing mechanism due to the interaction of the particles with one another and to interruption of flaws by the particles themselves. These particulate reinforced composite resins are stronger than microfill resins. As with the dispersion reinforced composites, the resin matrix typically includes methacrylate monomers. However, the filler in particulate reinforced composites has a greater impact on the total strength of the composite. Therefore, particulate reinforced composites are typically used for stress bearing restorations.

Another class of dental composites, known as hybrid composites, include the features and advantages of dispersion reinforcement and those of particulate reinforcement. Hybrid composite resins contain fillers having an average particle size of 0.6 µm or greater with a microfiller having an average particle size of about 0.05 µm or less. HERCULITE® XRV (Kerr Corp.) is one such example. HERCULITE® is considered by many as an industry standard for hybrid composites. It has an average particle size of 0.84 µm and a filler loading of 57.5% by volume. The filler is produced by a wet milling process that produces fine particles that are substantially contaminant free. About 10% of this filler exceeds 1.50 µm in average particle size. In clinical use, the surface of HERCULITE® turns to a semi-glossy matte finish over time. Because of this, the restoration may become distinguishable from normal tooth structure when dry, which is not desirable for a cosmetic restoration.

Another class of composites, flowable composites, typically have a volume fraction of structural filler of about 10% to about 30% by volume. These flowable composites are mainly used in low viscosity applications to obtain good adaptation and to prevent the formation of gaps during the filling of a cavity.

Various methods of forming submicron particles, such as precipitation or sol gel methods, are available to produce particulate reinforcing fillers for hybrid composites. However, these methods do not restrict the particle size to at or below the wavelength of light to produce a stable glossy surface. In U.S. Pat. No. 6,121,344, which is incorporated by reference herein in its entirety, a resin-containing dental composite is described including a structural filler of ground particles having an average particle size of between about 0.05 µm and about 0.5 µm that has the high strength required for load-bearing restorations, yet maintains a glossy appearance in clinical use required for cosmetic restorations. Because the structural filler particles are ground, the particles are nonspherical, providing increased adhesion of the resin to the structural filler, thereby further enhancing the overall strength of the composite. Through the use of structural filler particles that are ground and that have an average particle size less than the wavelength of light, that is less than about 0.50 µm, the dental composite exhibits the luster and translucency required for cosmetic restorations. Specifically, because the structural filler size is less than the wavelength of visible light, the surface of a dental restoration will reflect more light in some directions than in others even after wear of the composite by brushing. The visible light waves do not substantially interact with the structural filler particles protruding out of the surface of the composite, and therefore, haze is reduced and the luster of the surface is maintained even after substantial brushing. The particles are still large enough to reinforce the composite by the particulate reinforcement mechanism, so the restorations are also stress bearing. The number of larger particles, above 0.5 µm in diameter, are also minimized to help produce the stable glossy surface.

In U.S. Pat. No. 6,121,344, fumed silica microfill particles having an average particle size less than about 0.05 µm are added, preferably between about 1% by weight and about 15% by weight of the composite. The microfill particles contribute to dispersion reinforcement, fill the interstices between the larger structural filler particles reducing occluded volume, and provide a large surface area to be wetted by the resin to increase strength. The fumed silica microfill particles also contribute to the flow properties of the uncured resin. Fumed silicas are produced by hydrolysis of silicon tetrachloride vapor in a flame of hydrogen and oxygen. During this process, silicon dioxide molecules condense to form particles of size usually less than 50 nm.

The particles then attach to each other and sinter together. Due to the nature of the flame process, a three-dimensional chain aggregate with a length of 200–300 nm forms. Further mechanical entanglement occurs upon cooling to give agglomerates. Attractive interactions between the surface silanol groups of the particles give thixotropic properties to liquids in which these fumed silicas are suspended. The fumed silicas are hydrophobically treated to make them compatible with resins employed, but still substantial interactions result from attractive interactions of the residual silanol groups that are not reacted. The particle-particle interaction prevents homogenous dispersion of the microfiller in the resin matrix and increases the viscosity of the suspension, which correspondingly decreases the workability of the composite paste. This places a limitation on the practical filler loading in fumed silica microfilled restorative composites. A high filler loading is desirable in dental restorations because the high loading provides a paste with improved handling properties over a paste with low filler loading. Moreover, higher loading gives a composite that after curing is lower in shrinkage, has a coefficient of thermal expansion better matching that of a natural tooth and has higher overall physical properties.

There is thus a need to develop a dental restorative composite that has minimal particle-particle interactions to afford high filler loading and lower viscosity contribution when suspended in methacrylate resin.

SUMMARY OF THE INVENTION

The present invention provides a resin-containing dental composite including a structural filler of ground particles having an average particle size of between about 0.05 μm and about 0.5 μm and a nanofiller having discrete, non-agglomerated particles of mean particle size less than about 100 nm. The dental composite of the present invention has the high strength required for load-bearing restorations, yet maintains a glossy appearance in clinical use required for cosmetic restorations. Because the structural filler particles are ground, the particles are nonspherical, providing increased adhesion of the resin to the structural filler, thereby further enhancing the overall strength of the composite. Through the use of structural filler particles that are ground and that have an average particle size less than the wavelength of light, that is less than about 0.50 μm, the dental composite of the present invention provides the luster and translucency required for cosmetic restorations. The discrete, non-agglomerated nanofill particles contribute to dispersion reinforcement, fill the interstices between the larger structural filler particles reducing occluded volume, and provide a large surface area to be wetted by the resin to increase strength. Moreover, particle-particle interactions are minimized, thereby allowing for high filler loading and lower shrinkage upon curing.

DETAILED DESCRIPTION OF THE INVENTION

The present invention, in a preferred form, is a dental restorative composite which includes a ground structural filler having a mean particle size between about 0.05 μm and about 0.50 μm and a nanofiller having a mean particle size less than about 100 nm in a curable resin, preferably a polymerizable resin containing methacrylate monomers. Curing of the composite may be achieved by mixing two paste components containing a catalyst and accelerator, respectively, or by a photopolymerization process wherein the resins are cured when exposed to actinic radiation, such as blue visible light. Photopolymerizable resins containing monomers other than methacrylates may be used in the present invention, as may be appreciated by those skilled in the art, such as cationically photocurable oxiranes, for example. The dental composite is applied to teeth by the dental practitioner and, for example, exposed to a visible light source to cure the resin. The cured resin has a flexural strength higher than 100 MPa which allows for the use of the resin in stress bearing applications.

To provide ground structural filler having a mean particle size of less than 0.5 μm, an extensive comminution step is required. Comminution may be performed in an agitator mill, and preferably an agitator mill designed to minimize contamination, such as that described in U.S. Pat. No. 6,010,085, incorporated herein by reference in its entirety. Alternatively, comminution may be performed in a vibratory mill, and preferably in a vibratory mill designed to minimize contamination, such as described in U.S. Pat. Nos. 5,979,805 and 6,098,906, each incorporated herein by reference in its entirety. Comminution deagglomerates the structural filler particles by separating particles from clusters, decreases the size of the structural filler particles, eliminates large particles by breakage and increases the specific surface area of the structural filler particles by producing a large quantity of very fine particles. Size reduction with an agitator mill or vibratory mill occurs due to a combination of impact with the milling media, abrasion with the milling media and attrition of the particles.

Structural fillers suitable for use in the present invention include barium magnesium aluminosilicate glass, barium aluminoborosilicate glass (BAG), amorphous silica, silica-zirconia, silica-titania, barium oxide, quartz, alumina and other inorganic oxide particles. The mean particle size of the structural filler is limited to less than the wavelength of light to prevent the structural filler from decreasing surface gloss after substantial brushing. However, it is expected that as the particle size is reduced below about 1 μm the strength needed for load-bearing restorations demises due to increasing occluded volume of resin. Currently, it is believed that a mean particle size between about 0.05 μm and about 0.5 μm provides the best balance between optical and structural properties.

Nanofillers suitable for use in the present invention include powders with particles that are not aggregated or substantially agglomerated so as to minimize particle-particle interactions. The discrete particles have a mean particle size less than 100 nm. By "discrete particles," there are included weakly agglomerated particles having an agglomerated average size less than 100 nm. For example, Nanomaterials Research Corp., Longmonte, Colo., manufactures an aluminosilicate powder having a mean particle size of about 80 nm and a 1:4 molar ratio of alumina to silica. This nanofiller has a refractive index of 1.508. The powder is produced by a thermal quench process using a plasma torch for vaporization, such as described in U.S. Pat. Nos. 5,984,997; 5,851,507; and 5,788,738, each incorporated by reference herein in its entirety. The powder produced by the plasma or thermal quench process using a gas phase precursor includes discrete, non-agglomerated particles of narrow particle size distribution.

By way of further example, Nanophase Technologies Corp., Romeoville, Ill., manufactures gamma alumina powders having mean particle sizes less than 20 nm, as well as a powder having a mean particle size of 38 nm. This nanofiller has a refractive index of about 1.71. The powder is produced by a physical vapor synthesis process, such as described in U.S. Pat. Nos. 5,874,684; 5,514,349; and 5,460,701, each incorporated by reference herein in its entirety.

The nanofiller particles may be surface treated, for example with gamma methacryloxypropyltrimethoxy silane (MEMO). The nanofiller comprises at least about 0.01% by volume of the dental composite, more advantageously about 1–15% by volume, and most advantageously about 5–12% by volume.

Generally, the nanofiller should have a refractive index similar to that of the resin. Resins typically have a refractive index of about 1.48–1.55. Thus, the nanofiller should have a refractive index in the range of about 1.48–1.6. However, it is believed that for nanofillers of 20 nm particle size or less, the refractive index may vary from that of the filler without negatively affecting the optical properties of the dental composite. Thus, for gamma alumina nanofiller, the particle size is preferably 20 nm or less due to its relatively high refractive index.

EXAMPLE 1

To prepare the structural filler for inclusion into the dental composite, the filler material to be milled, in this case BAG (barium aluminoborosilicate glass, type SP-345, Specialty Glass, Oldsmar, Fla.), was charged into a vibratory mill from Sweco (Florence, Ky.), as described in U.S. Pat. Nos. 5,979,805 and 6,098,906, incorporated herein by reference in their entirety. The vibratory mill was filled with glass media and water, and the mill was vibrated to comminute the particles.

When the filler slurry is removed from the mill, the mean particle size is measured, typically by laser scattering. Laser scattering is a method of measuring mean particle size by sensing the average relative angular intensity of scattered light. A beam of monochromatic light with a uniform wave front is directed at the sample, the light is diffracted or scattered by the particles and a detector is used to measure the relative average intensity of the scattered light at various angles. The mean particle size and size distribution may then be calculated from the relative average intensity. One such laser scattering device is disclosed in U.S. Pat. No. 5,610,712 to Schmitz et al., incorporated herein by reference in its entirety. For the present example, a Horiba Model 2A-910 Laser Scattering Mean Particle Size Analyzer was used. The resulting structure filler is as follows: 10% by volume of the filler particles have a mean particle size of less than 0.28 µm; 50% by volume of the filler particles have a mean particle size less than 0.44 µm; and 90% by volume of the filler particles have a mean particle size less than 0.66 µm. This filler is referred to henceforth as a 0.4 µm structural filler.

The slurry was then dried at 110° C. and the dried cake was sieved through a 100 mesh (150 µm) plastic screen. The ground glass was then silanated by spraying in a V-blender with a 20% hydrolyzed solution of MEMO in water to make the powder hydrophobic. The loading of the silane in the filler was 2.5% by weight.

The properly sized structural filler, in this example the 0.4 µm structural filler, is combined with nanofiller particles in accordance with the present invention, such as gamma alumina or aluminosilicates having a mean particle size less than 100 nm. These nanopowders were first treated with 5% MEMO by slurring the components in ethanol and adding 0.1% n-propylamine as catalyst and drying at 110° C. overnight. For comparison, the structural filler is also combined with a mixture of two types of hydrophobic fumed silica, TS530 or US202 (each available commercially from Degussa Corp., Ridgefield Park, N.J.), having an average particle size of 20 nm and OX-50 (also available commercially from Degussa Corp., Ridgefield Park, N.J.) having an average particle size of 40 nm. The OX-50 was silanated by spraying in a V-blender with a 20% hydrolyzed solution of MEMO in water to make the powder hydrophobic. The loading of the silane in the OX-50 was 5% by weight.

The 0.4 µm structural filler and the nanofillers are then combined with a light-curable resin base material which may include commercially available monomers containing methacrylate groups. TABLE 1 lists the components of the resins that will be used in later examples. Pigments such as titanium dioxide may be added to control optical properties of the composite.

TABLE 1

RESIN COMPOSITIONS

| COMPONENT | Resin 1 (Wt. %) | Resin 2 (Wt. %) | Resin 3 (Wt. %) |
|---|---|---|---|
| BisGMA (Bisphenol A Diglycidyl ether dimethacrylate) | 3.0 | — | — |
| Ethoxylated Bisphenol A Dimethacrylate (No. of ethoxy groups = 3.5) | 71.1 | — | — |
| Ethoxylated Bisphenol A Dimethacrylate (No. of ethoxy groups = 2.0) | — | 88.9 | — |
| Urethane Dimethacrylate | — | — | 79.0 |
| Triethylene Glycol Dimethacrylate | 24.7 | — | 19.8 |
| Hexane Diol Dimethacrylate | — | 9.9 | — |
| 2-Ethylhexyl-4-(dimethylamino)benzoate | 0.49 | 0.49 | 0.49 |
| Camphorquinone | 0.17 | 0.17 | 0.17 |
| 2-Hydroxy-4-methoxy Benzophenone | 0.49 | 0.49 | 0.49 |
| Butylated Hydroxytoluene (BHT) | 0.05 | 0.05 | 0.05 |
| TOTAL | 100 | 100 | 100 |
| Viscosity, η* at 25° C. (Pa · s) | 0.15 | 0.30 | 0.50 |
| Refractive Index | 1.518 | 1.532 | 1.479 |

Other monomers may be used in the resin composition, such as diethylene glycol dimethacrylate, tetraethylene glycol dimethacrylate, 1,12-dodecanediol dimethacrylate, diurethane dimethacrylate (Rohamere 6661-0, Huls America, Somerset, N.J.), trimethylolpropane trimethacrylate, glyceryl dimethacrylate, and neopentylglycol dimethacrylate.

The resin is introduced into a planetary mixer thermostated at 50° C. A polycaprolactone-modified methacrylate monophosphate dispersant was added to the resin in an amount of 2 wt. % in accordance with U.S. patent application Ser. No. 09/306,628 filed May 6, 1999, incorporated by reference herein in its entirety. Specifically, a polycaprolactone-modified glycerol dimethacrylate dispersant was used, which was prepared with a 5:1 molar ratio of caprolactone units to glycerol dimethacrylate. The planetary mixer is then started and the filler containing the physically admixed components listed in TABLE 2 are added slowly over a period of three hours. The composite is subsequently mixed for another hour and then de-aerated under attenuated oxygen pressure. Control Samples 1 and 2 included a mixture of prior art fumed silicas, specifically OX-50 and US202 fillers. Test Samples 1 and 2 included discrete nanofillers in accordance with the present invention, specifically 38 nm gamma alumina from Nanophase Technologies Corp. and 80 nm 1:4 molar ratio aluminosilicate from Nanomaterials Research Corp.

EXAMPLE 2

For comparative purposes, similar composites were prepared using the same method, but substituting a 1.0 µm structural filler system for the 0.4 µm filler used in Example 1. Control Samples 3 and 4 included the prior art TS530 fumed silica instead of the US202 filler, and Control Sample 3 did not include a dispersant. TABLE 3 lists the components used in Example 2.

In forming a restoration using the composite of the present invention, the surface of the tooth is prepared by removing any portion of the tooth enamel, and if necessary the dentin, that is decayed or damaged. A retention groove is then formed in the dentin if needed to maintain the restoration on the tooth. The practitioner then adds opacifiers and pigments to match the color of the composite with the color of the tooth. The composite is then built up on the surface of the tooth to replace any lost material. Once the practitioner is satisfied with the appearance of the restoration the composite is exposed to a visible light source to cure the resin and activate the adhesive by cross-linking the polymer matrix. After the composite has been cured, the surface is polished.

Testing

The results are provided in Tables 2 and 3. All measurements were carried out using standard ISO methods except where indicated, and the standard deviations are provided in parentheses. Standard ISO method 4049 for resin-based filling materials was used whenever possible.

TABLE 2

| Resin | Control 1<br>Resin 2 | Test 1<br>Resin 2 | Control 2<br>Resin 1 | Test 2<br>Resin 1 |
|---|---|---|---|---|
| Wt % Nanofiller (Vol. %) | 4% OX-50 + 4% US202 (7.2) | 11.6% Alumina[1] (7.0) | 4% OX-50 + 4% US202 (7.2) | 12.4% 1:4 Aluminosilicate[1] (10.1) |
| Wt % 0.4 μm BAG[2] filler (Vol. %) | 67 (47.6) | 69 (54.2) | 67 (47.6) | 67 (50.5) |
| Wt % Dispersant | 2 | 2 | 2 | 2 |
| Wt % Load including nanofiller + BAG[2] filler (Vol. %) | 75 (54.8) | 80.6 (61.2) | 75 (54.8) | 79.4 (60.6) |
| % Translucency[3] | 37.8 | 20.4 | 38.2 | 41 |
| % Contrast Ratio[4] | 60.7 | 83.9 | 59.7 | 56.1 |
| Vicker's Hardness[5] (N/mm$^2$) | 534 (9) | 700 (4) | 517 (7) | 667 (7) |
| Flexural Strength (MPa) | 119 (10) | 135 (10) | 119 (12) | 121 (20) |
| Flexural Modulus (MPa) | 10180 (648) | 12919 (956) | 9718 (413) | 11739 (434) |
| % Axial shrinkage at 60 sec[6] | 2.05 (0.07) | 1.69 (0.02) | 2.59 (0.06) | 2.26 (0.02) |
| % Axial shrinkage at 10 sec[6] | 1.66 (0.06) | 1.22 (0.03) | 1.91 (0.06) | 1.69 (0.04) |
| % Axial shrinkage at 5 sec[6] | 1.33 (0.02) | 0.77 (0.04) | 1.38 (0.02) | 1.24 (0.05) |
| Penetrometer (mm) 0 g, 1 mm flathead[7] | 3.2 | 1.6 | 5.1 (3/21) | 2.5 |

[1]5% MEMO coated.
[2]BAG-Barium Aluminosilicate Glass.
[3]Samples 20 mm in diameter and 1 mm in thickness were cured on each side for 60 seconds with a tungsten halogen lamp. The translucency was then measured in the transmission mode using a TCS Colorimeter (BYK-Gardner, Columbia, MD), by recording the Y value after the sample was placed on the transmission accessory.
[4]The same sample as from note 3 was placed against a white background and the Y value was measured using an X-Rite spectrophotometer (Grandville, MI). A measurement against a black background was also obtained and the ratio of the Y values was multiplied by 100 and is called the contrast ratio.
[5]Average of 3 measurements on the top surface of a cylindrical sample 10 mm in diameter and 2 mm in height. The samples were light cured for 40 seconds and stored in water for 24 hours at 37° C. prior to measurement.
[6]The bonded disk method of D. C. Watts and A. J. Cash (Dent. Mater. 7, 281 (1991)) was used. A 1.8 mm disk-shaped sample of paste is sandwiched between a cover glass plate 1.8 mm thick and a glass cover slip of 0.2 mm in diameter. A non-contact brass ring-shaped spacer is used. On top, an LDVT transducer with a 2 g probe mass is in contact with the glass slip and measures the dimensional change after polymerization for 20 seconds from a Demetron 500 dental curing light with an 11 mm tip situated underneath the glass plate. The measurement agter 5, 10 and 60 seconds is recorded.
[7]Precision Penetrometer (GCA Corp., Chicago, IL) with a 1 mm flat head was used with no additional weight (0 g). The paste was placed in a mold 10 mm in diameter and 8 mm in height. Penetration was performed for 10 seconds. An average of 3 measurements is reported.

TABLE 3

| Resin | Control 3<br>Resin 1 | Test 3<br>Resin 1 | Control 4<br>Resin 3 | Test 4<br>Resin 3 |
|---|---|---|---|---|
| Wt % Nanofiller (Vol. %) | 4% OX-50 + 4% TS530 (7.3) | 10.4% 38 nm Alumina[1] (6.4) | 4% OX-50 + 4% TS530 (7.7) | 10.4% 80 nm 1:4 Aluminosilicate[1] (8.8) |
| Wt % 1.0 μm BAG[2] filler (Vol. %) | 68 (48.8) | 72 (57.7) | 72 (54.1) | 72 (56.2) |
| Wt % Dispersant | 0 | 2 | 2 | 2 |
| Wt % Load including nanofiller + BAG filler (Vol. %) | 76 (56.1) | 82.4 (64.1) | 80 (61.8) | 82.4 (65.0) |
| % Translucency | 40.7 | 24.5 | 33.3 | 39.4 |
| % Contrast Ratio | 57.2 | | 66.6 | 58.2 |

TABLE 3-continued

| Resin | Control 3 Resin 1 | Test 3 Resin 1 | Control 4 Resin 3 | Test 4 Resin 3 |
|---|---|---|---|---|
| Vicker's Hardness (N/mm$^2$) | 592 (2) | 682 (9.5) | 648 (7) | 728 (13) |
| Flexural Strength (MPa) | 131 (11) | 142 (16) | 155 (12) | 149 (13) |
| Flexural Modulus (MPa) | 11293 (568) | 13379 (362) | 11995 (730) | 13583 (345) |
| % Axial shrinkage at 60 sec | 2.66 (0.08) | 1.98 (0.06) | 2.03 (0.1) | 1.83 (0.03) |
| % Axial shrinkage at 10 sec | 1.99 (0.1) | 1.24 (0.02) | 1.51 (0.04) | 1.39 (0.01) |
| % Axial shrinkage at 5 sec | 1.28 (0.06) | 0.68 (0.06) | 1.08 (0.01) | 1.02 (0.04) |
| Penetrometer (mm) 0 g, 1 mm flathead | 3.1 | 3.3 | 2.7 | 3.1 |

[1]5% MEMO coated.
[2]BAG-Barium Aluminosilicate Glass.
[3]Samples 20 mm in diameter and 1 mm in thickness were cured on each side for 60 seconds with a tungsten halogen lamp. The translucency was then measured in the transmission mode using a TCS Colorimeter (BYK-Gardner, Columbia, MD), by recording the Y value after the sample was placed on the transmission accessory.
[4]The same sample as from note 3 was placed against a white background and the Y value was measured using an X-Rite spectrophotometer (Grandville, MI). A measurement against a black background was also obtained and the ratio of the Y values was multiplied by 100 and is called the contrast ratio.
[5]Average of 3 measurements on the top surface of a cylindrical sample 10 mm in diameter and 2 mm in height. The samples were light cured for 40 seconds and stored in water for 24 hours at 37° C. prior to measurement.
[6]The bonded disk method of D. C. Watts and A. J. Cash (Dent. Mater. 7, 281 (1991)) was used. A 1.8 mm disk-shaped sample of paste is sandwiched between a cover glass plate 1.8 mm thick and a glass cover slip of 0.2 mm in diameter. A non-contact brass ring-shaped spacer is used.
On top, an LDVT transducer with a 2 g probe mass is in contact with the glass slip and measures the dimensional change after polymerization for 20 seconds from a Demetron 500 dental curing light with an 11 mm tip situated underneath the glass plate. The measurement after 5, 10 and 60 seconds is recorded.
[7]Precision Penetrometer (GCA Corp., Chicago, IL) with a 1 mm flat head was used with no additional weight (0 g). The paste was placed in a mold 10 mm in diameter and 8 mm in height. Penetration was performed for 10 seconds. An average of 3 measurements is reported.

For dental composites containing both the 0.4 µm structural filler and the 1.0 µm structural filler, the substitution of alumina nanoparticles of 38 nm average particle size for the fumed silica led to a reduction in translucency, an increase in hardness and flexural modulus and strength, and a significant reduction in shrinkage. Substitution of aluminosilicate nanoparticles of 80 nm average particle size for the fumed silica led to an increase in translucency, hardness and flexural modulus, and a small reduction in shrinkage. For the 0.4 µm structural filler with nanoparticles in accordance with the present invention, lower viscosity was achieved, as evidenced by the penetrometer measurements.

The tests described above used small-scale prepared pastes and the formulas were not especially optimized with respect to the extent of mixing. More intense mixing methods and variations in the nanoparticle surface treatment are expected to further increase volume loading of the fillers, which is likewise expected to lead to further reduction in shrinkage. The reduction in shrinkage observed in the above examples is believed to be attributable to the higher volume loading. Higher loading is made possible by the reduction in occluded volume of the resin with the discrete nanoparticles leading to fewer high density microregions in the polymerized composite. Also, it should be understood that the translucency of a paste increases typically upon aging due to "wetting out" of the filler. This "wetting out" effect is expected to be more pronounced with nanofillers due to the smaller inclusions between them for which the resin takes longer to enter.

Thus, the dental composite of the present invention provides a restoration having the high strength useful for load-bearing restorations, and also provides translucency and surface gloss useful in cosmetic restorations. The gloss is apparent even after substantial wear as can be observed in a recall appointment 6 months or longer after the placement of the restoration. Through the use of structural filler particles having a mean particle size less than the wavelength of light, yet large enough to provide strength, the dental composite of the present invention provides the luster and translucency of dispersion reinforced composites with the strength of hybrid composites. Through the use of discrete, non-aggregated nanoparticles, improved physical properties may be obtained, and less shrinkage occurs upon polymerization.

While the present invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details and representative composition as shown and described. This has been a description of the present invention, along with the preferred composition using the present invention as currently known. However, the invention itself should only be defined by the appended claims.

What is claimed is:
1. A dental composite, comprising:
a polymerizable resin base; and
about 10% by volume to about 80% by volume filler consisting essentially of a ground structural filler and a non-ground nanofiller,
wherein the ground structural filler comprises between about 10% by volume and about 70% by volume of the composite and consists of ground particles of mean particle size between about 0.05 μm and about 0.50 μm, and wherein the ground structural filler contains less than 50% by volume of particles above 0.5 μm in diameter, and wherein the non-ground nanofiller comprises between about 1.0% by volume and about 15% by volume of the composite and consists essentially of discrete, non-aggregated gamma alumina particles having a mean particle size of about 40 nm or less.

2. The dental composite of claim 1, wherein the resin composite, in the cured form, has a flexural strength of at least 100 MPa.

3. The dental composite of claim 2, wherein the resin composite, in the cured form, has a flexural strength of at least 120 Mpa.

4. The dental composite of claim 1, wherein the resin base comprises a polymerizable vinyl compound.

5. The dental composite of claim 1, wherein the ground structural filler contains less than 10% by volume of particles above 0.8 μm in diameter.

6. The dental composite of claim 1, wherein the non-ground nanofiller comprises between about 5 and about 12% by volume of the composite.

7. The dental composite of claim 1, wherein the non-ground nanofiller has a refractive index in the range of about 1.48 to about 1.6.

8. A dental composite comprising:

a polymerizable resin base; and about 11% by volume to about 80% by volume filler in the resin base, the filler consisting essentially of a ground structural filler and a non-ground nanofiller, wherein the ground structural filler comprises between about 10% by volume and about 70% by volume of the composite and consists of ground particles having a mean particle size of between about 0.05 μm and about 0.50 μm, and wherein the non-ground nanofiller comprises between about 1.0% by volume and about 15% by volume of the composite and consists essentially of discrete, non-aggregated aluminosilicate particles having a mean particle size of less than about 100 nm, and a 1:4 molar ratio of alumina to silica.

9. The dental composite of claim 8, wherein the resin composite, in the cured form, has a flexural strength of about 120 MPa or greater.

10. The dental composite of claim 8, wherein the resin base includes a polymerizable vinyl compound.

11. The dental composite of claim 8, wherein the non-ground nanofiller comprises between about 5% by volume to about 12% by volume of the composite.

12. The dental composite of claim 8, wherein the aluminosilicate particles have a mean particle size of about 80 nm.

13. The dental composite of claim 8, wherein the resin composite, in the cured form, has a flexural strength of at least 100 MPa.

14. The dental composite of claim 8, wherein the ground structural filler contains less than 10% by volume of particles above 0.8 μm in diameter.

15. The dental composite of claim 8, wherein the non-ground nanofiller has a refractive index in the range of about 1.48 to about 1.6.

* * * * *

UNITED STATES PATENT AND TRADEMARK OFFICE
Certificate

Patent No. 6,593,395 B2          Patented: July 15, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Christos Angeletakis, Orange, CA; Minh-Dang Son Nguyen, Orange, CA; and Alvin I. Kobashigawa, Fountain Valley, CA.

Signed and Sealed this Fourth Day of November 2003.

VASU JAGANNATHAN
*Supervisory Patent Examiner*
Art Unit 1714

UNITED STATES PATENT AND TRADEMARK OFFICE
CERTIFICATE OF CORRECTION

| | | |
|---|---|---|
| PATENT NO. | : 6,593,395 B2 | |
| APPLICATION NO. | : 09/859106 | |
| DATED | : July 15, 2003 | |
| INVENTOR(S) | : Christos Angeletakis, Minh-Dang Son Nguyen and Alvin I. Kobashigawa | |

It is certified that error appears in the above-identified patent and that said Letters Patent is hereby corrected as shown below:

Title Page and Column 1, line 1, Title of Patent reads "DENTAL COMPOSITION CONTAINING..." and should read -- DENTAL COMPOSITE CONTAINING... --.

Column 2, line 53 reads "...in diameter, are also minimized..." and should read -- ...in diameter, is also minimized... --.

Column 8, line 48, in TABLE 2, footnote 6 reads "The measurement agter 5, 10 and 60 seconds is recorded." and should read -- The measurement after 5, 10 and 60 seconds is recorded. --.

Column 8, line 65, in TABLE 3, under the header "Resin" reads "% Translucency" and should read -- % Translucency$^3$ -- *(superscript number missing)*.

Column 8, line 66, in TABLE 3, under the header "Resin" reads "% Contrast Ratio" and should read -- % Contrast Ratio$^4$ -- *(superscript number missing)*.

Column 9, line 6, in TABLE 3, under the header "Resin" reads "Vicker's Hardness" and should read -- Vicker's Hardness$^5$ -- *(superscript number missing)*.

Column 9, line 13, in TABLE 3, under the header "Resin" reads "60 sec" and should read -- 60 sec$^6$ -- *(superscript number missing)*.

Column 9, line 15, in TABLE 3, under the header "Resin" reads "10 sec" and should read -- 10 sec$^6$ -- *(superscript number missing)*.

Column 9, line 17, in TABLE 3, under the header "Resin" reads "5 sec" and should read -- 5 sec$^6$ -- *(superscript number missing)*.

Column 9, line 19, in TABLE 3, under the header "Resin" reads "1 mm flathead" and should read -- 1 mm flathead$^7$ -- *(superscript number missing)*.

UNITED STATES PATENT AND TRADEMARK OFFICE
CERTIFICATE OF CORRECTION

PATENT NO. : 6,593,395 B2
APPLICATION NO. : 09/859106
DATED : July 15, 2003
INVENTOR(S) : Christos Angeletakis, Minh-Dang Son Nguyen and Alvin I. Kobashigawa It is certified that error appears in the above-identified patent and that said Letters Patent is hereby corrected as shown below:

Column 11, line 16 reads "... at least 120 Mpa." and should read -- ... at least 120 MPa. --.

Signed and Sealed this

Twenty-sixth Day of June, 2007

JON W. DUDAS
*Director of the United States Patent and Trademark Office*